United States Patent [19]

Doorakian et al.

[11] 4,177,216

[45] Dec. 4, 1979

[54] NOVEL TRIBUTYL (2,5-DIHYDROXYPHENYL)PHOSPHONIUM HYDROXIDE INNER SALTS

[75] Inventors: George A. Doorakian, Waltham; Lawrence G. Duquette, Maynard, both of Mass.

[73] Assignee: The Dow Chemical Company, Midland, Mich.

[21] Appl. No.: 945,945

[22] Filed: Sep. 26, 1978

Related U.S. Application Data

[60] Division of Ser. No. 674,019, Apr. 5, 1976, Pat. No. 4,132,706, which is a continuation of Ser. No. 481,599, Jun. 21, 1974, abandoned.

[51] Int. Cl.$^2$ .................................................. C07F 9/54
[52] U.S. Cl. .............................. 260/606.5 F; 562/594; 562/598; 562/602; 562/605; 562/607
[58] Field of Search ................. 260/606.5 F, 606.5 N; 562/607, 602, 605, 598, 594

[56] References Cited

U.S. PATENT DOCUMENTS 4,093,650   6/1978   Doorakian ................ 260/606.5 F X

OTHER PUBLICATIONS

Ramirez et al., J.A.C.S. 78 5614 (1956).
Arshad et al., Chem. Abstracts. 73 65576u (1970).

*Primary Examiner*—Helen M. S. Sneed
*Attorney, Agent, or Firm*—L. Wayne White; Michael L. Glenn

[57] ABSTRACT

The trisubstituted (2,5-dihydroxyphenyl)phosphonium hydroxide inner salts and their hydrolyzed derivatives are novel latent catalysts for promoting reaction between vicinal epoxides and phenols and/or carboxylic acids (or anhydrides). Precatalyzed epoxy resins are easily prepared using such catalysts.

5 Claims, No Drawings

NOVEL TRIBUTYL (2,5-DIHYDROXYPHENYL)PHOSPHONIUM HYDROXIDE INNER SALTS

This is a divisional of application Ser. No. 674,019 filed Apr. 5, 1976 now U.S. Pat. No. 4,132,706 which is a continuation of application Ser. No. 481,599 filed June 21, 1974 now abandoned.

BACKGROUND OF THE INVENTION

1. Field of the Invention

This invention pertains to novel latent catalysts for promoting reaction between vicinal epoxides and phenols and/or carboxylic acids (or anhydrides of such acids). Such reactions are commercially important in that functional monomers (e.g. hydroxyethyl acrylate), hydraulic fluids (e.g. 2-phenoxyethanol) and high molecular weight linear or cross-linked epoxy resins are thus produced.

2. Description of the Prior Art

The reactions between epoxides and phenols and/or carboxylic acids (or anhydrides) have been extensively studied and many patents have issued which describe these well known classes of reactants. See, for example, U.S. Pat. Nos.:

| | | |
|---|---|---|
| 2,216,099 | 3,377,406 | 3,547,885 |
| 2,633,458 | 3,477,990 | 3,694,407 |
| 2,658,885 | 3,547,881 | 3,738,862 |

Canadian Pat. No. 893,191, German Pat. No. DT 2,206,218, and the text "Handbook of Epoxy Resins" by H. Lee and K. Neville, McGraw Hill, N.Y. (1967).

In addition to describing the classes of reactants, the above patents also show that (1) a catalyst is required to attain a satisfactory reaction rate and (2) those skilled in the art recognize that the reaction between epoxides and phenols is not, mechanistically speaking, the same as the reaction between epoxides and carboxylic acids (or anhydrides) due to the differences in products. The latter point is illustrated by the fact that substantially linear polymers are produced (U.S. Pat. No. 3,477,990) by reacting epoxy resins with polyfunctional phenols in the presence of a catalyst whereas cross-linked polymers are produced (U.S. Pat. No. 3,547,885) by reacting the same epoxy resins with a polycarboxylic acid (or anhydride) in the presence of the same catalysts. The reactive species which catalyzes the reaction is therefore believed to be different in each instance. Thus, compounds which catalyze one reaction would not necessarily be expected to catalyze the other.

Several problems have been encountered in using many of the prior art catalysts. In many instances, the catalysts react with the epoxy reactant and thus preclude the option of marketing a blend comprising an epoxy resin and a catalyst; this blend is commonly referred to as a "precatalyzed epoxy resin". In other instances, the problem associated with the prior art catalysts is selectivity; i.e. the catalysts simultaneously promote the reaction between the epoxy reactant and the phenolic hydroxyl group (or acid group) on the reactant and the aliphatic hydroxyl group(s) on the product giving branched or cross-linked polymers rather than the desired linear polymers. In still other instances, the reaction rate is unsatisfactory and/or the product is highly colored and therefore unsatisfactory for many uses and/or the product was contaminated with corrosive anions (e.g. chloride) and is therefore unacceptable for electrical encapsulationf (potting).

These and other problems have now been solved by the subject invention.

SUMMARY OF THE INVENTION

It has now been discovered that the trisubstituted (2,5-dihydroxyphenyl)phosphonium hydroxide inner salts, and the hydrolyzed derivatives thereof, are novel latent catalysts for promoting the reaction between vicinal epoxides and phenols and/or carboxylic acids (or anhydrides).

The novel catalysts are surprisingly effective in selectively catalyzing the desired reaction between the reactants at a suitable reaction rate. The reaction products are obtained in high yields and are of generally excellent color.

Additionally, the novel catalysts are surprisingly unreactive with epoxy resins at conventional storage temperatures. As a result, precatalyzed epoxy resins can now be produced by merely blending the subject catalysts with the epoxy resins. Such precatalyzed epoxy resins are, of course, novel compositions of matter.

THE NOVEL CATALYSTS

The trisubstituted (2,5-dihydroxyphenyl)phosphonium hydroxide inner salts correspond to formula I below

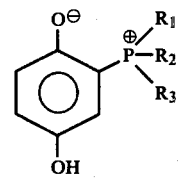

wherein $R_1$–$R_3$ are hydrocarbyl or inertly-substituted hydrocarbyl radicals, each of which independently has from 1 to about 20 carbon atoms. $R_1$, $R_2$, and $R_3$ are preferably each n-butyl or phenyl and are most preferably n-butyl.

The hydrolyzed derivatives of formula I correspond to formula II

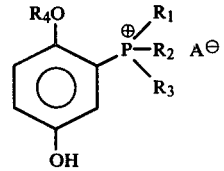

wherein $R_1$–$R_3$ have the aforesaid values; $R_4$ is hydrogen, benzyl or lower alkyl (1 to 6 carbon atoms); and $A^\ominus$ is a compatible neutralizing anion (such as chloride, bromide, iodide, bisulfate, chlorosulfonate, acetate, diacetate, trifluoromethylsulfonate, trifluoroacetate, adipate, acrylate, chloroacetate, trichloroacetate, etc.). The non-nucleophilic anions (such as bisulfate, acetate, diacetate, adipate, etc.) are preferred anions for precatalyzed resins. Bromide and iodide anions are the preferred nucleophilic anions. In formula II, $R_1$–$R_3$ are likewise preferably each n-butyl or phenyl and are most preferably n-butyl. $R_4$ is preferably hydrogen.

Compounds of formula I are prepared by reacting 1,4-benzoquinone with a tertiary phosphine

in an inert solvent (e.g. benzene) and filtering off the product.

Compounds of formula II are prepared by reacting the corresponding compound of formula I with a Bronsted acid ($H^{\oplus}A^{\ominus}$) or with an alkyl or benzyl chloride or bromide. The anion of any particular compound of formula II can be exchanged for another anion by conventional anion exchange techniques.

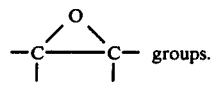
groups.

The alkylene oxides of from 2 to about 24 carbon atoms, the epihalohydrins and the epoxy resins are perhaps the best known and most widely used members of the genus. Ethylene oxide, 1,2-propylene oxide, 1,2-butylene oxide and epichlorohydrin are the preferred monoepoxides. There are two preferred subclasses of epoxy resins. The first subclass corresponds to the general formula

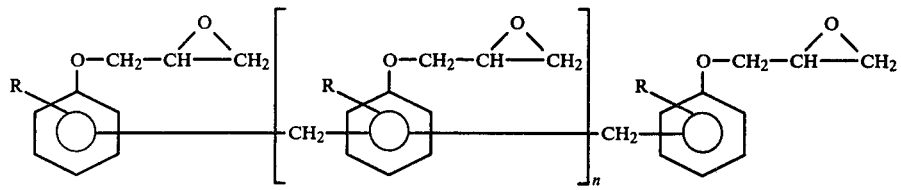

Illustrative examples of the instant class of catalysts include those of formulas I and II wherein $R_1$–$R_3$ are methyl, ethyl, n-butyl, hexyl, octyl, decyl, dodecyl, octadecyl, phenyl, tolyl, 4-octylphenyl, 3,5-dimethylphenyl, benzyl, phenethyl, phenylbutyl, 3,5-dimethylbenzyl, cyclohexyl, allyl, hydroxymethyl, cyanoethyl, 2-cyanopropyl, and the like. Other illustrative examples include those of formulas I and II in which $R_1$–$R_3$ are different. For example, those in which $R_1$ is n-butyl, $R_2$ is phenyl and $R_3$ is phenyl; those in which $R_1$ is hexyl, $R_2$ is tolyl, and $R_3$ is benzyl; and other like variations.

In certain applications the presence of an anion $A^{\ominus}$ may be undesirable. For example, the coating of metal substrates with a high molecular weight epoxy resin is one such instance where hard anions (such as chloride) are undesirable due to corrosion problems. In those instances, compounds of formula I will have an advantage of the compounds represented by formula II.

The above compounds are particularly useful in catalyzing the reaction between vicinal epoxides and phenols and/or carboxylic acids. In this utility, the amount used can be varied over a wide range. Generally, however, they are used in a small but catalytic amount, as for example in amounts of from about 0.001 to about 10 percent by weight, based on the combined weight of reactants. Preferably, the catalyst is included in amounts of from about 0.05 to about 5 percent by weight.

THE EPOXY REACTANTS

As stated above, the reactants here used are well known classes of compounds.

The vicinal epoxides, for example, are organic compounds bearing one or more wherein R is hydrogen or an alkyl radical and n is from about 0.1 to about 10, preferably from about 1 to about 2. Preparation of these polyepoxides is illustrated in U.S. Pat. No. 2,216,099 and U.S. Pat. No. 2,658,885. The second subclass corresponds to the general formula

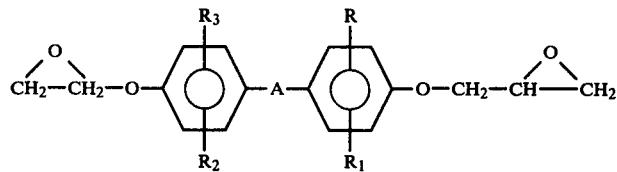

wherein R, $R_1$, $R_2$ and $R_3$ are independently selected from hydrogen, bromine and chlorine and wherein A is an alkylene (e.g. methylene) or alkylidene (e.g. isopropylidene) group having from about 1 to about 4 carbon atoms,

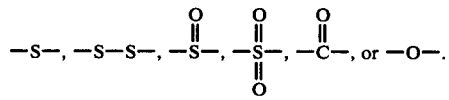

THE PHENOLIC REACTANTS

The phenols are organic compounds having one or more hydroxyl groups attached to an aromatic nucleus. This class of compounds therefore includes phenol, alpha and beta-naphthol, o-, m-, or p-chlorophenol, alkylated derivatives of phenol (e.g. o-methyl-, 3,5-dimethyl-, p-t-butyl- and p-nonylphenol) and other monohydric phenols as well as polyhydric phenols, such as resorcinol, hydroquinone, etc. The polyhydric phenols bearing from 2 to 6 hydroxyl groups and having from 6 to about 30 carbon atoms are particularly useful in the reaction with epoxy resins to form high molecular weight resins (linear or cross-linked) useful in coatings. Particularly preferred polyhydric phenols are those corresponding to the formula

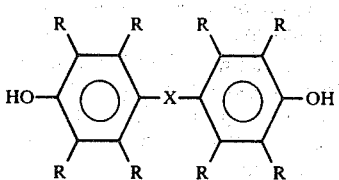

wherein R is hydrogen, halogen (fluoro, chloro or bromo) or hydrocarbyl and X is oxygen, sulfur, —SO—, —SO$_2$—, bivalent hydrocarbon radicals containing up to 10 carbon atoms, and oxygen, sulfur and nitrogen-containing hydrocarbon radicals, such as —OR'O—, —OR'OR'O—, —S—R'—S—, —S—R'—S—R'—S—, —OSiO—,

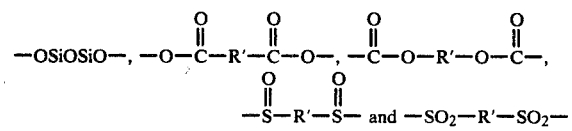

radicals wherein R' is a bivalent hydrocarbon radical. 4,4'-Isopropylidenediphenol (i.e. bisphenol A) is the most preferred phenol).

THE CARBOXYLIC ACID REACTANTS

The organic carboxylic acids and anhydrides are likewise well known. The acids bear one or more carboxyl groups on the organic nucleus. The anhydrides are prepared from such carboxylic acids by the removal of water therefrom in an intra- or intermolecular condensation. This class of compounds therefore includes acetic, propionic, octanoic, stearic, acrylic, methacrylic, oleic, benzoic, phthalic, isophthalic, maleic, succinic, adipic, itaconic, polyacrylic and polymethacrylic acids, and the like, and anhydrides thereof, such as acetic anhydride, phthalic anhydride, hexahydrophthalic anhydride, etc.

There are two subclasses of carboxylic acids and anhydrides that are particularly important based on their reaction with epoxy resins.

The reaction of ethylenically unsaturated monocarboxylic acids with epoxy resins produces hydroxy-substituted esters or polyesters which are particularly useful in the preparation of coatings, adhesives, etc. See, for example, U.S. Pat. No. 3,377,406. Acrylic and methacrylic acid are particularly useful in this regard. Accordingly, the ethylenically unsaturated monocarboxylic acids are a preferred subclass of acids.

The second preferred subclass of acids is comprised of members which are useful in cross-linking epoxy resins. The members of this subclass are normally di- or tribasic acids, or anhydrides thereof, and are preferably liquid or low-melting solids, such as succinic, maleic or hexahydrophthalic acids or anhydrides and the like. Other such acids and anhydrides are shown, for example, in U.S. Pat. Nos. 2,970,983 and 3,547,885.

RATIO OF REACTANTS

The ratio of vicinal epoxide reactant to phenol and/or carboxylic acid reactant in the subject process can vary over a wide range depending upon the product desired. E.g. if a product terminated with a phenolic ether group is desired, obviously one would employ an excess of phenol in the process, etc.

SOLVENTS

In many instances the reactants are liquid and no solvent or diluent is needed. In other cases, however, where one or both of the reactants are solid or viscous liquids, an inert solvent or diluent can be used advantageously. Suitable such inert solvents or diluents are known to those skilled in the art and include ketones (such as acetone, methyl ethyl ketone, etc.), hydrocarbons (such as benzene, toluene, xylene, cyclohexane, ligroin, etc.) and the like.

OTHER PROCESS PARAMETERS

Generally, the reaction mixture is warmed at temperatures in the range of from about 50° C. to about 225° C. (preferably 100°–175° C.) until an exotherm begins and, after the exotherm has peaked, substantially warmed in the same range for an additional time to assure substantially complete reaction. Atmospheric or superatmospheric pressure (e.g. up to about 200 psig) are common.

THE REACTION PRODUCTS

The products here produced are generally known compounds in industry. The particular product produced will vary in properties depending upon the selection and ratio of reactants used in the process. Every combination of reactants of course need not be discussed but the following discussion will illustrate the types of products which can be produced.

The reaction products here produced by reacting an epoxy resin with a phenol in the presence of the subject catalysts are phenolic ethers bearing one or more aliphatic secondary hydroxyl groups. Such aliphatic hydroxyl groups are formed in the ring-opening reaction between the oxirane and phenolic hydroxyl groups. Additionally, the reaction products bear a terminal epoxy group(s) or a phenolic hydroxyl group(s) depending upon the ratio of reactants. Consequently, they are reactive intermediates which can be cured (crosslinked) with many polyfunctional curing agents to form hard, insoluble solids which are useful coatings. A list of several known curing agents which are suitable for use herein is found in U.S. Pat. No. 3,477,990. The cured products (particularly those of high molecular weight) are useful as surface coatings, as adhesive layers in laminates, coatings on filament windings, in structural binding applications, and the like. The reaction products prepared from halogenated (particularly brominated) phenols are particularly useful in flameproofing applications since they tend to be self-extinguishing. Thus, they are useful in forming cured coatings for wood paneling and as adhesive layers in wood laminates, etc.

The reaction products here produced by reacting an epoxy resin with a monocarboxylic acid (or anhydride of such acids) have terminal ester groups and are useful in coatings, adhesives, reinforced plastics, moldings, etc. The reaction products formed by reacting epoxy resins with polycarboxylic acids, or anhydrides thereof, are cross-linked insoluble resins used in coatings, etc.

Functional monomers are here produced by reacting a $C_2$ to $C_4$ alkylene oxide with acrylic or methacrylic acid. Hydraulic fluids are here prepared by reacting lower alkylene oxide with a phenol in substantially equimolar amounts. Nonionic surfactants are here prepared by reacting an alkylated monohydric phenol with a $C_2$ to $C_4$ alkylene oxide, or mixture of such alkylene oxides.

Other useful products can be similarly prepared by the reaction of vicinal epoxides with phenols and/or carboxylic acids (or anhydrides) in the presence of the subject catalysts.

The following examples further illustrate the invention:

EXPERIMENTS 1-7

This series of experiments was conducted by charging to a reaction vessel (equipped with a thermometer and mechanical stirrer and prepurged with nitrogen) a diglycidyl ether of bisphenol A having an epoxy equivalent weight of 187 (4.5 g.), bisphenol A (2.628 g.) and 0.011 g. of the phosphonium catalyst dissolved in methanol. The reaction mixture was warmed up to about 150° C. after which the heat was turned off. An exotherm was observed in each instance and after the exotherm subsided, the reaction mixture was heated at 160° C. for an additional 3 hours. The results of the experiments are shown in Table 1. All of the resins produced were of excellent color.

TABLE I

Epoxy Catalyst Screening Results to Prepare Linear High Molecular Weight Epoxy Resins

| Experiment No. | Catalyst | Theoretical Percent Epoxide | Actual % Epoxide Remaining |
| --- | --- | --- | --- |
| 1 | 4-hydroxyphenyl(triphenyl)phosphonium phenoxide (inner salt); phenoxide $O^-$, $P^+$—$(C_6H_5)_3$, para-OH | 2.00 | 2.04 |
| 2 | 4-hydroxyphenyl(tri-n-butyl)phosphonium phenoxide; $O^-$, $P^+$—$(n\text{-}C_4H_9)_3$, para-OH | 2.00 | 2.00 |
| 3 | 4-ethoxyphenyl structure with $OC_2H_5$, $P^+$—$(C_6H_5)_3$ $I^-$, para-OH | 2.00 | 2.05 |
| 4 | di-OH phenyl, $P^+$—$(C_6H_5)_3$ $HSO_4^-$ | 2.00 | 2.94 |
| 5 | di-OH phenyl, $P^+$—$C_6H_5)_3$ $^-O\text{—}\underset{\underset{O}{\|\|}}{C}\text{—}CH_3$ | 2.00 | 2.04 |
| 6 | di-OH phenyl, $P^+$—$(C_6H_5)_3$ $^-O_3S\text{—}C_6H_4\text{—}CH_3$ | 2.00 | 2.85 |
| 7 | di-OH phenyl, $P^+$—$(C_6H_5)_3$ $Br^-$ | 2.00 | 2.20 |

EXPERIMENTS 8-14

This series of experiments was conducted in an analogous fashion except that here we used 2.812 g. of bisphenol A in each instance and the reaction mixtures were heated at 160° C. for 5 hours instead of the 3 hours used above. The results are summarized in Table II.

nol A in each instance and the reaction mixtures were heated at 160° C. for only 1.5 hours instead of the times used heretofore. The results are summarized in Table III.

TABLE II

Epoxy Catalyst Screening Results to Prepare Linear High Molecular Weight Epoxy Resins

| Experiment No. | Catalyst | Theoretical Percent Epoxide | Actual % Epoxide Remaining |
|---|---|---|---|
| 8 | 2,5-dihydroxyphenyl-P$^+$(C$_6$H$_5$)$_3$ with O$^-$ at position 1 | 1.00 | 1.21 |
| 9 | 2,5-dihydroxyphenyl-P$^+$(n-C$_4$H$_9$)$_3$ with O$^-$ at position 1 | 1.00 | 1.11 |
| 10 | 2-ethoxy-5-hydroxyphenyl-P$^+$(C$_6$H$_5$)$_3$ I$^-$ | 1.00 | 1.26 |
| 11 | 2,5-dihydroxyphenyl-P$^+$(C$_6$H$_5$)$_3$ HSO$_4^-$ | 1.00 | 2.47 |
| 12 | 2,5-dihydroxyphenyl-P$^+$(C$_6$H$_5$)$_3$ $^-$O–C(=O)–CH$_3$ | 1.00 | 1.20 |
| 13 | 2,5-dihydroxyphenyl-P$^+$(C$_6$H$_5$)$_3$ $^-$O$_3$S–C$_6$H$_4$–CH$_3$ | 1.00 | 2.37 |
| 14 | 2,5-dihydroxyphenyl-P$^+$(C$_6$H$_5$)$_3$ Br$^-$ | 1.00 | 1.36 |

EXPERIMENTS 15–31

This series of experiments was conducted in analogous fashion except that here we used 1.698 g. of bisphenol

TABLE III

Epoxy Catalyst Screening Results to Prepare Linear High Molecular Weight Epoxy Resins

| Experiment No. | Catalyst | Theoretical % Epoxide | Actual % Epoxide Remaining |
|---|---|---|---|
| 15 | 2-(tri-n-butylphosphonio)-4-hydroxyphenolate (phenoxide with P⊕–(n-C$_4$H$_9$)$_3$, para OH) | 8.00 | 7.90 |
| 16 | 2-(triphenylphosphonio)-4-hydroxyphenyl ethyl ether iodide (OC$_2$H$_5$, P⊕–(C$_6$H$_5$)$_3$, I⊖, para OH) | 8.20 | 8.28 |
| 17 | 2-(triphenylphosphonio)-1,4-dihydroxyphenyl chloride (OH, P⊕–(C$_6$H$_5$)$_3$, Cl⊖, para OH) | 8.20 | 8.31 |
| 18 | 3-(tri-n-butylphosphonio)-1,4-dihydroxyphenyl (HO, P⊕–(nC$_4$H$_9$)$_3$, HO) | 8.00 | 7.65 |
| 19 | same phosphonium as 18 with CF$_3$CO$_2$⊖ | 8.00 | 7.95 |
| 20 | same phosphonium as 18 with ClCH$_2$CO$_2$⊖ | 8.00 | 8.09 |
| 21 | same phosphonium as 18 with CH$_2$=CH–CO$_2$⊖ | 8.00 | 8.29 |
| 22 | 3-(triphenylphosphonio)-1,4-dihydroxyphenyl with ⊖O$_2$C–(CH$_2$)$_4$–CO$_2$H | 8.00 | 7.94 |
| | 3-(triphenylphosphonio)-1,4-dihydroxyphenyl with CF$_3$CO$_2$⊖ | | |
| 23 | 3-(triphenylphosphonio)-1,4-dihydroxyphenyl with NO$_3$⊖ | 8.00 | 8.58 |

TABLE III-continued
Epoxy Catalyst Screening Results to Prepare Linear High Molecular Weight Epoxy Resins

| Experiment No. | Catalyst | Theoretical % Epoxide | Actual % Epoxide Remaining |
|---|---|---|---|
| 24 | 2,4-dihydroxyphenyl-P⁺(C₆H₅)₃ with CH₂=CH—CO₂⁻ | 8.00 | 8.27 |
| 25 | 2,4-dihydroxyphenyl-P⁺(C₆H₅)₃ | 8.00 | 8.21 |
| 26 | 2,4-dihydroxyphenyl-P⁺(C₆H₅)₃ with ClCH₂CO₂⁻ | 8.00 | 8.06 |
| 27 | 4-hydroxyphenoxide-P⁺[(CH₂)₇CH₃]₃ with Cl₃CCO₂⁻ | 8.00 | 7.94 |
| 28 | 4-hydroxyphenoxide-P⁺(CH₂—CH₂—CN)₃ | 8.00 | 8.07 |
| 29 | 2,4-dihydroxyphenyl-P⁺[(CH₂)₇CH₃]₃ with ⁻O—C(=O)—CF₃ | 8.00 | 7.62 |
| 30 | 2,4-dihydroxyphenyl-P⁺(CH₂CH₂CN)₃ with ⁻O—C(=O)—CF₃ | 8.00 | 7.65 |
| 31 | 2,4-dihydroxyphenoxide-P⁺(CH₂OH)₃ | 8.00 | 10.75 |

Experiments 1–31 demonstrate that the instant catalysts are particularly good latent catalysts for promoting the reaction between epoxy resins and phenols.

EXPERIMENTS 32–37

In this series of experiments an epoxy resin having an epoxy equivalent weight of 172–178 (100.0 g.) and hexahydrophthalic anhydride (80.0 g.) and the instant catalyst (0.15 g.) were thoroughly mixed and maintained under a vacuum for at least 15 minutes or until bubbling under vacuum was very slight. The reaction mixture was then warmed at 110° C. for 2 hours, the heat turned off and the exotherm allowed to subside. The reaction mixture was then heated at 150° C. for an additional 2 hours (12 hours for Experiment 18) and cooled. In every instance, the cured product was clear, colorless and very hard. The catalysts are described in Table IV.

TABLE IV

Catalyst Screening Results to Cross-Link Epoxy Resins with Anhydrides

| Experiment No. | Catalyst |
|---|---|
| 32 | OH—C₆H₄(OH)—P⁺(C₆H₅)₃ HSO₄⁻ |
| 33 | (HO)₂C₆H₃—P⁺(C₆H₅)₃ ⁻O—C(=O)—CH₃ |
| 34 | CH₃CH₂—O—C₆H₃(OH)—P⁺(C₆H₅)₃ I⁻ |
| 35 | ⁻O—C₆H₃(OH)—P⁺(C₆H₅)₃ |
| 36 | (HO)₂C₆H₃—P⁺(C₆H₅)₃ CH₃—C₆H₄—SO₃⁻ |
| 37 | ⁻O—C₆H₃(OH)—P⁺(n-C₄H₉)₃ |

In a companion series of experiments, aliquots of the above mixtures were maintained for two weeks at room temperature prior to curing and no appreciable change in the viscosity of the uncured mixtures was noted.

Similar good results were noted in another series of experiments wherein the hexahydrophthalic anhydride used in the above formulations was replaced with dodecenylsuccinic and nadic methyl anhydrides but longer cure schedules were required.

Experiments 32–37 demonstrate that the instant catalysts are particularly effective as latent catalysts in promoting the reaction between epoxy resins and anhydrides.

Similarly, the instant catalyst would be useful in promoting the reaction between epoxy resins and blends of phenols and carboxylic acids and/or anhydrides.

The cured products from Experiments 1–37 strongly adhered to the reaction vessel and were useful as protective coatings.

Other species of the instant catalyst can be similarly used. In addition, modifications of the above experiments can be made. For example, the above anhydrides can be replaced with other anhydrides such as maleic anhydride leading to cross-linked products. Alternatively, acrylic or methacrylic acid could be used in the reaction conditions leading to epoxy resins terminated with a free-radical or thermally polymerizable vinyl groups. Such compounds are likewise useful as coating materials.

Other such variations of the instant invention will be readily apparent to one of ordinary skill in the art.

We claim:

1. A tri-n-butyl(2,5-dihydroxyphenyl)phosphonium hydroxide inner salt or a hydrolyzed derivative thereof corresponding to the formula

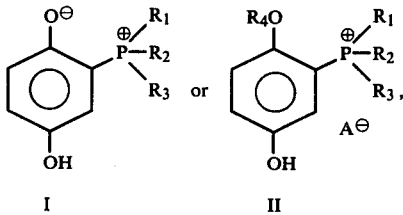

wherein $R_1$–$R_3$ are each n-butyl, $R_4$ is hydrogen, benzyl or lower alkyl, and $A^\ominus$ is a compatible neutralizing anion.

2. The compound defined by claim 1 wherein $A^\ominus$ is bromide, iodide or a non-nucleophilic anion.

3. The compound defined by claim 1 wherein $R_4$ is hydrogen.

4. A hydrolyzed derivative of a tri-n-butyl(2,5-dihydroxyphenyl)phosphonium hydroxide inner salt corresponding to the formula

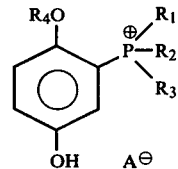

wherein $R_1$–$R_3$ are each n-butyl, $R_4$ is hydrogen, benzyl or lower alkyl and $A^\ominus$ is a compatible non-nucleophilic neutralizing anion, and wherein said non-nucleophilic anion is bisulfate, acetate, diacetate, chloroacetate, trifluoroacetate, acrylate or adipate.

5. The compound defined by claim 4 wherein the non-nucleophilic anion is chloroacetate and $R_4$ is hydrogen.

* * * * *